US012102331B2

(12) United States Patent
Walzman (10) Patent No.: US 12,102,331 B2
(45) Date of Patent: Oct. 1, 2024

(54) SINGLE LUMEN MICROCATHETER FOR EXECUTING PLUGS NEAR DISTAL TERMINUS OF LUMEN

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 1059 days.

(21) Appl. No.: 16/779,514

(22) Filed: Jan. 31, 2020

(65) Prior Publication Data

US 2020/0178982 A1 Jun. 11, 2020

Related U.S. Application Data

(63) Continuation-in-part of application No. 15/731,804, filed on Aug. 3, 2017, now Pat. No. 10,575,856.

(60) Provisional application No. 62/600,137, filed on Feb. 13, 2017.

(51) Int. Cl.
*A61B 17/12* (2006.01)
*A61M 25/00* (2006.01)
*A61M 25/10* (2013.01)

(52) U.S. Cl.
CPC .. *A61B 17/12186* (2013.01); *A61B 17/12109* (2013.01); *A61M 25/007* (2013.01); *A61B 2017/1205* (2013.01); *A61M 2025/0018* (2013.01); *A61M 25/0075* (2013.01); *A61M 25/10* (2013.01); *A61M 2205/0266* (2013.01)

(58) Field of Classification Search
CPC ............ A61M 25/007; A61M 25/0075; A61M 25/0074; A61M 2025/0076; A61M 2025/0073; A61M 2025/0018; A61B 17/12181; A61B 17/12159; A61B 2090/037
See application file for complete search history.

(56) References Cited

U.S. PATENT DOCUMENTS

| | | |
|---|---|---|
| 4,755,176 A | 7/1988 | Patel |
| 4,784,638 A | 11/1988 | Ghajar et al. |
| 4,970,926 A | 11/1990 | Ghajar et al. |
| 5,180,387 A | 1/1993 | Ghajar et al. |
| 5,380,276 A | 1/1995 | Miller et al. |
| 5,800,407 A | 9/1998 | Eldor |
| 5,954,687 A | 9/1999 | Baudino |
| 6,223,637 B1 | 5/2001 | Hansen |
| 6,569,145 B1 | 5/2003 | Shmulewitz |
| 8,403,911 B2 | 3/2013 | Adams et al. |
| 8,496,629 B2 | 7/2013 | McKinnon et al. |
| 9,364,634 B2 | 6/2016 | Adams et al. |
| 9,399,112 B2 | 7/2016 | Shevgoor et al. |
| 9,440,043 B2 | 9/2016 | Arora et al. |
| 2007/0073271 A1 | 3/2007 | Brucker |
| 2008/0183128 A1 | 7/2008 | Morriss |

(Continued)

OTHER PUBLICATIONS

International search report for international application PCT/US20/62486 mailed Mar. 10, 2021.
European Search Report EP 20917233 Dated: Jan. 25, 2024.

*Primary Examiner* — Scott J Medway
*Assistant Examiner* — Anh Bui (57) ABSTRACT

A device using side holes which creates a plug upstream of the distal-most portion of said micro-catheters and thereby ameliorates the suboptimal outcomes associated with creating a plug upstream of a distal end hole via injecting embolics only at the distal-most portion of said catheters.

24 Claims, 7 Drawing Sheets

(56) References Cited

U.S. PATENT DOCUMENTS

| | | |
|---|---|---|
| 2010/0036410 A1 | 2/2010 | Krolik |
| 2010/0049165 A1* | 2/2010 | Sutherland ....... A61B 17/12109 |
| | | 604/529 |
| 2011/0251545 A1* | 10/2011 | Duffy ...................... A61L 27/14 |
| | | 604/522 |
| 2013/0310687 A1 | 11/2013 | Takizawa |
| 2014/0039459 A1 | 2/2014 | Folk |
| 2015/0088100 A1 | 3/2015 | Oborn |
| 2015/0119674 A1 | 4/2015 | Fischell et al. |
| 2015/0174381 A1 | 6/2015 | Morita |
| 2015/0209550 A1* | 7/2015 | Teh ................... A61M 25/0069 |
| | | 604/523 |
| 2018/0049747 A1 | 2/2018 | Tal et al. |
| 2018/0104443 A1 | 4/2018 | Walzman |
| 2018/0228494 A1* | 8/2018 | Walzman .......... A61M 25/0074 |
| 2019/0001113 A1 | 1/2019 | Call |
| 2019/0329000 A1 | 10/2019 | Tal et al. |
| 2020/0016310 A1* | 1/2020 | Spears .................. A61M 1/267 |

\* cited by examiner

SINGLE LUMEN MICROCATHETER FOR EXECUTING PLUGS NEAR DISTAL TERMINUS OF LUMEN

BACKGROUND OF THE INVENTION

Field of the Invention

This invention relates in general to medical equipment and procedures. In particular, the invention relates to catheters for use in performing certain medical procedures, such as the treatment of brain arteriovenous malformations includes endovascular embolization, surgical resection, and stereotactic radiotherapy, alone or in combination.

The present invention is a tool to more safely and more effectively implement endovascular treatment of arteriovenous malformations and arteriovenous fistulas, reducing procedural times and exposure to X-ray radiation to the patient and the treating staff.

Background Art

Treatment of brain arteriovenous malformations includes endovascular embolization, surgical resection, and stereotactic radiotherapy, alone or in combination. In the past, n-butyl cyanoacrylate (nBCA) was used as an adjunct to surgery; however, introduction of a dimethyl sulfoxide (DMSO)-based embolic agent, Onyx (ev3, Covidien), and more recently in other countries, PHIL™ (Precipitating Hydrophobic Injectable Liquid, MicroVention® Terumo) and SquidPERI (EVOH, by emboflu, Switzerland), and advancement in micro-catheter design often offered better endovascular results in brain arteriovenous malformations treatment. Liquid embolic agents are the preferred embolic material in endovascular treatment of pial and brain arteriovenous malformations and dural arteriovenous fistulas. Advancements in micro-catheter design and emergence of new embolic agents offer better results in endovascular treatment of brain arteriovenous malformations.

Among said advances is the use of dual lumen devices which employ one lumen to dispense a balloon to block Onyx flow and a second lumen to deploy Onyx. Said prior art teaches that double-lumen versions are more efficient than single-lumens because double-lumen allow simultaneous execution of tasks.

The reduction from two lumens (note: for medical devices, a luminous term referring to the channel within a tube) to one is non-obvious. In particular, the prior art related to lumens teaches that double-lumen versions are more effective single-lumens for managing unexpected as well as anticipated difficulties. Additionally, the prior art related to lumens teaches that double-lumen versions are more efficient than single-lumens because double-lumen allow simultaneous execution of tasks. Thus, the prior art teaches away from reducing lumens generally and specially teaches away from single-lumens.

The prior art contains several catheters with a hole in addition to the end hole. Most of these are taught by twelve patents: U.S. Pat. No. 9,440,043 (Arora et al.); U.S. Pat. Nos. 9,399,112; 9,364,634; 8,496,629; 8,403,911; 6,223,637; 5,954,687; 5,800,407; 5,180,387; 4,970,926; 4,784,638; and 4,755,176.

However, most are designed to drain cerebrospinal fluid from the ventricular through a catheter that enters through a hole in the skull and would not be capable of injecting glue into an artery that enters through the femoral artery and is snaked up through blood vessels in the body. Additionally, the inventions described in said patents could be used to inject something directly into the brain and/or ventricle. However, they could not be used to inject something into an artery within the brain, or to provide a temporary arterial bypass. If it were introduced directly into the artery through the brain it would undoubtedly cause a life-threatening bleed in the brain. The medical basis is that a catheter designed to be inserted directly into the brain has no possible role for an intravascular application.

Additionally, the structure of the devices taught by said twelve patent differs from the structure of the present invention. In particular, U.S. Pat. No. 9,440,043, which is a catheter having a tapered structure and balloon formed above a lower drainage hole differ from the present invention because it has a balloon which covers the distal end hole and the present invention does not. U.S. Pat. No. 9,399,112 is a catheter hole having an inclined trailing edge while the present invention does not have an angled side hole. U.S. Pat. No. 9,364,634 teaches an embedded co-extrusion for improving catheter hole array efficiency, whereas the present invention does not use co-extrusions. U.S. Pat. No. 8,496,629 is a catheter which uses staggered diffusion holes a flow breaking feature, the present invention does not require any flow breaking feature. Similarly, U.S. Pat. No. 8,403,911 uses diffusion side holes to improve catheter efficiency, while the present invention does not require any flow breaking feature, including diffusion side holes. U.S. Pat. No. 6,223,637 is a catheter side-wall hole cutting apparatus, whereas the present invention while capable of deploying a device to cut a catheter side-wall has neither a suction element nor a cutting element. U.S. Pat. No. 5,954,687 teaches the use of a fluid reservoir, however the present inventions does not. U.S. Pat. No. 5,800,407 is a multiple hole epidural catheter which teaches the use of both permanently opened and permanently closed holes, whereas the present inventions uses holes which can be both opened and closed on a temporary basis in addition to holes which are permanently open. Furthermore, the present invention is designed for intravascular, not epidural use. U.S. Pat. No. 5,180,387 teaches the use of angled holes in a catheter with a non-circular bore, the present invention teaches non-angled holes in a circular bore.

U.S. Pat. No. 4,970,926 teaches an apparatus for making angled hole ventricular catheter which uses a plurality of rods with an end hole in each, where as the present invention teaches the use of side holes. The '638 shows an angled hole ventricular catheter designed for extended impartment in the brain, whereas the present invention does not use angled holes and is not intended for extended impartment in the brain. U.S. Pat. No. 4,755,176 teaches a catheter with side hole in one of two lumens, whereas the present invention is a single lumen device.

The art prior to the inventor's other disclosures suffers from several significant shortcomings. These include difficulty forming a proximal "plug" before too much distal Onyx prevents a subsequent ejective distal "push", too much reflux of Onyx along the micro-catheter, approaching a normal branch artery, necessitating aborting that injection for safety concerns. Other shortcomings include slow plug formation, and the need for longer procedures necessitating longer fluoroscopic times and higher radiation doses.

The prior art also fails to adequately address the fact that during the initial "plug" injection(s) of Onyx 34 (after lacing the micro-catheter with dimethyl sulfoxide) are off target. Consequently, some of the plug material ends up in the distal most tip of the micro-catheter (beyond the side hole). Additionally, typically the plugging material, such Onyx 34, when in contact with blood that is not moving will then start to solidify in the tip of the micro-catheter, and can obstruct it. An obstructed, distal penetration of the lesion being treated with the embolics agent is no longer possible An improved liquid embolic agent delivery system is required to ameliorate said difficulties. It appears that the present invention is an excellent alternative to existing embolic agent delivery systems because it allows said ameliorations. In particular, it is easier to use than existing delivery systems, allows faster plug formation, and requires less procedural time and X-ray/radiation dosage; it is also more consistently effective.

Said micro-catheters and embolic agents often require creating a plug at the distal-most portion of said micro-catheters in order to facilitate optimal subsequent embolic penetration. Typically, treatments are suboptimal when there is difficulty forming a "plug". Said difficulties can result in liquid embolic failure to penetrate the target area, such as a fistula's nidus.

SUMMARY OF INVENTION

The present invention teaches how to create and use a device which facilitates creation of a plug or plug-equivalent near but proximal to the distal end hole of said micro-catheters, thereby ameliorating the difficulties in creating said plug utilizing current technologies.

The present invention is a single lumen micro-catheter with a single or multiple side holes a set short distance from the end hole (typically 5 mm-30 mm). The hole positioning is designed to allow the more viscous Onyx 34 (or higher viscosity versions of MicroVention's Precipitating Hydrophobic Inject-able Liquid, or similar liquid embolic agents) be delivered more proximately to a targeted location. This novel delivery would allow the formation of a proximal "plug" more easily.

As a result of such targeted delivery of a "plug", less viscous Onyx 18 (or similar) consequently can then be more easily "pushed" into an AVM nidus or another target lesion more effectively. This results in better distal lesion penetration, and less chance of unwanted proximal reflux.

Some embodiments of the present invention incorporate valve technology to control Onyx flow. Said valve technology uses either semi-permeable material to control of selected fluids by employing selectively permeable, or non-permeable material to control flow, or a combination. The selective flow control valve embodiment of the current invention can be set with fixed flow through area. The variable flow control valve embodiment of the current invention allows variable flow control area. Said variability of flow area is capable of responding to changes in pressure, fluid viscosity, magnetic field or combination thereof, or other differential conditions.

Some embodiments of the present invention incorporate differential inner diameter sizing of a catheter, together with a wire, to allow flow of liquids and/or liquid embolic through the majority of the catheter and out the distal "side hole", while preventing unwanted early filling of the distal-most portion of the catheter beyond the side hole.

For example, the micro-catheter up to the side hole may have an ID of 0.014", and beyond the side hole it may have an ID of 0.007". Once the micro-catheter is in the desired position for embolization, DMSO followed by Onyx 34 can be injected with a wire in the catheter to create a "plug" at the side hole. The wire completely obstructs the portion of the catheter distal to the side hole, which has an ID that matches the OD of the wire, thus preventing Onyx from entering that segment of the catheter before desired, and possibly hardening within that portion of the catheter and obstructing it. Once an adequate "plug" has been formed, the wire can be removed and Onyx 18 (or similar) can be "pushed" out the distal hole of the catheter and into the target lesion.

Another embodiment of the present invention does not have a side hole. Instead, at a similar location along the distal portion of the catheter, it has a thin layer of hydrogel adhered along the entire circumference of the catheter. The hydrogel can be such that it expands after a certain amount of time exposed to blood, or with a certain electrical magnetic signal, or with infusion of a certain triggering liquid, or other trigger. Once the catheter is in the desired position, the hydrogel can be expanded, and the hydrogel will act as a "plug" to prevent reflux of liquid embolic such as Onyx 18, when it is injected through the catheter and out the distal end hole.

All versions can have at least one "detachment" zone at a desired location, in some embodiments. In such embodiments, the end of the catheter near the distal end hole may detach after injection of liquid embolic, in certain circumstances, similar to the EV3/Medtronic Apollo detachable tip micro-catheter. In some embodiments, a wire may have a detachable segment. In some embodiments both the catheter and a wire may have at least one detachment zone, which when activated can effectively cut the distal end of the catheter and/or wire away from the more proximal segment.

DETAILED DESCRIPTION OF THE DRAWINGS

DETAILED DESCRIPTION OF THE INVENTION

Figure 1:
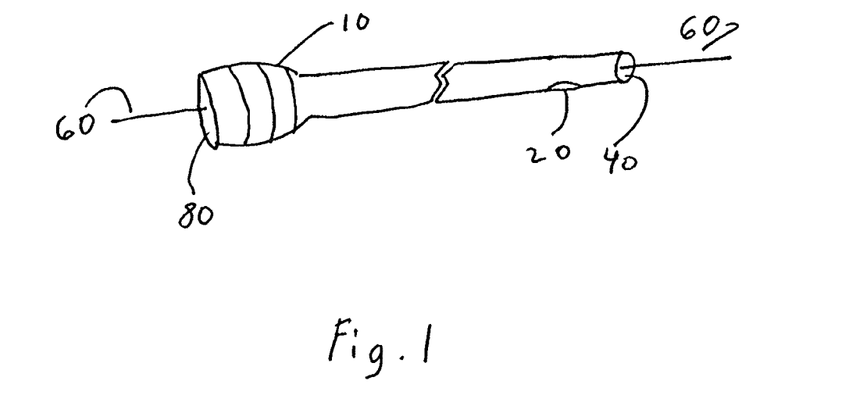
FIG. 1 is a side view of the single lumen catheter of the current invention depicting a side hole, untapered end, a distal end hole, proximal catheter hole, and an optional microwire.

The present invention uses an existing lumen element for a novel purpose. In particular, the present invention uses a hole on the side of a single-lumen micro-catheter (hereinafter "side hole") for preparing a plug. While use of at least one side hole has been taught, the teaching had several potential limitations, as described above. FIG. 1 depicts the most basic version of the catheter, untapered, with a single side hole, but no governing valve. Alternatively, there may be multiple circumferential holes disposed about the same segment of the catheter.

As used in the present disclosure, the terms proximal end hole to distal end of side hole(s) define a proximal catheter "segment". A proximal catheter "portion" is proximal to the end hole through a detachment site, and a distal catheter "portion" is from the detachment site through the end hole.

The novel use of side hole 20 is to build a plug proximal to the distal-most end hole 40 of the catheter. Said plug, when successfully deployed would prevent unwanted reflux of Onyx (or similar or equivalent), and would facilitate better distal penetration of the lesion. If there is unwanted proximal reflux, there can be flow of embolic material into normal branches more proximally, which can result in unwanted occlusion of said branch, tissue ischemia, disability and/or death. Said prevention of unwanted proximal flow ameliorates possible unwanted occlusions of normal vessels. Thus, the use is patentably novel.

The present invention can take several embodiments. Referring now to FIG. 1, the current invention is composed of a catheter 10, a side hole 20, a distal end hole 40, a proximal catheter hole 80, and a removeable wire 60 dimensioned to plug said distal end hole disposed within said lumen, wherein said detachment zone is a re-joinable coupling element capable of detachment from and reattachment to said catheter.

Figure 1A:
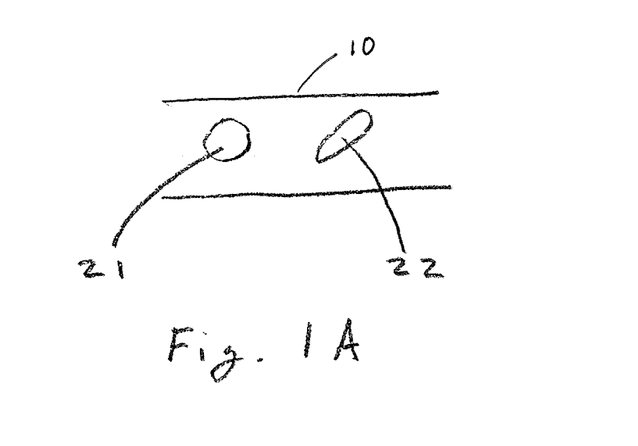
FIG. 1A shows a partial view of two embodiments of side hole 20.
Figure 2:
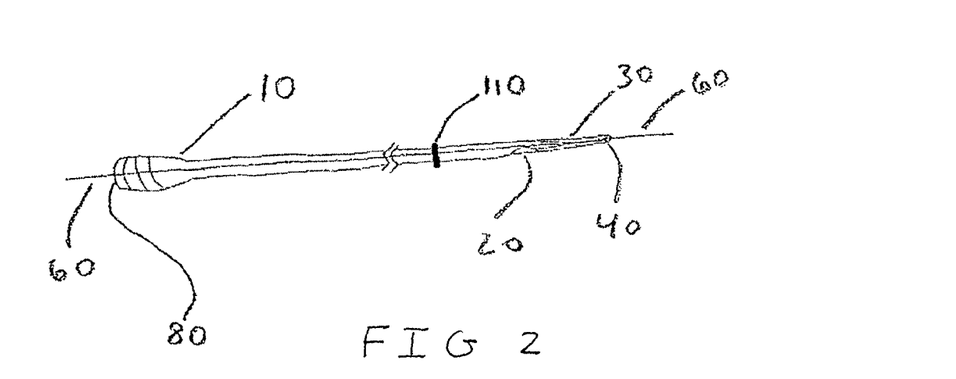
FIG. 2 depicts the embodiment of FIG. 1, further including a breakaway or detachment element near the proximal side of the side hole, and a tapered end.
Figure 2A:
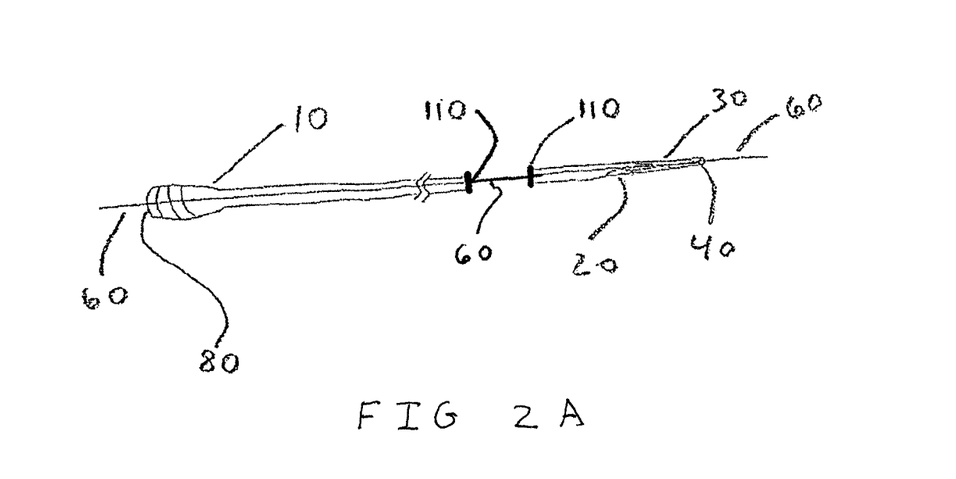
FIG. 2A depicts the embodiment of FIG. 2, further depicting optional microwire 60 disposed within breakaway or detachment element 110 in an uncoupled state.
Figure 3:
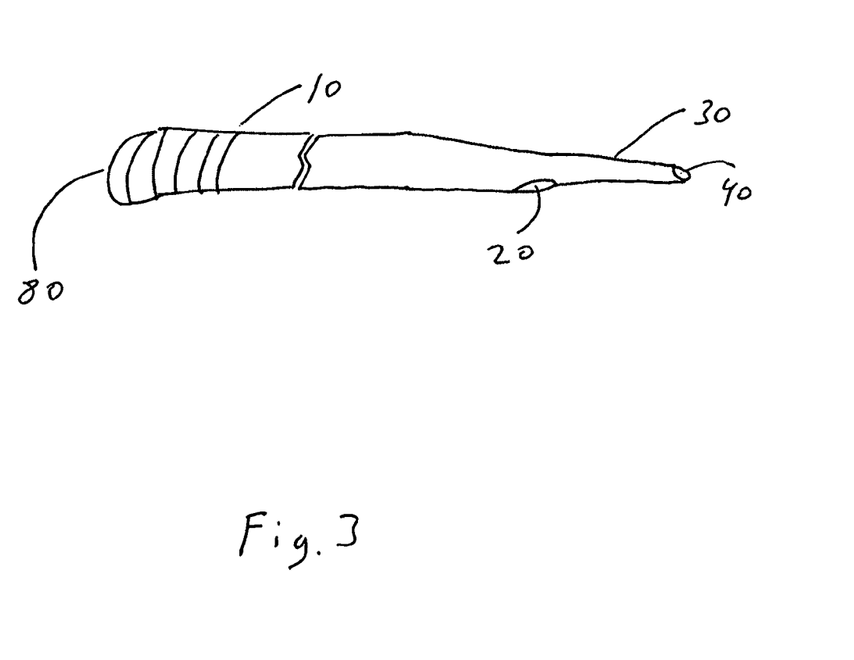
FIG. 3 depicts the embodiment of FIG. 2 without the optional microwire.

Referring now to FIG. 1A, side hole 20 may be perpendicular to catheter 10, such as perpendicular as depicted as side hole 21, or side hole 20 may be angled with respect to the longitudinal axis of catheter 10, as depicted by angled side hole 22. This embodiment takes a form similar to the design of the Transfrom (Stryker) and/or the Hyperglide/Hyperform (EV3/Covidien/Medtronic) balloon. FIG. 2 shows the embodiment of FIG. 1 with the addition of a detachment (or breakaway) element 110 between proximal end hole 80, side hole 20, and tapered end 30. Detachment element 110 may be a coupling, a score, a stressed area, or any other suitable means for detaching the distal end of catheter 10 using perpendicular force provided by the proximal end of the catheter 10. FIG. 3 shows the embodiment of FIG. 2 of the present invention without the wire 60.

However, the present invention as envisioned by embodying the general design of the Transform (Stryker) and/or the Hyperglide/Hyperform (EV3/Covidien/Medtronic) has no balloon enclosing contrast. It has a larger inner diameter until the end of the side hole, approximately 0.011 in., and smaller thereafter, approximately 0.008 in. Initial injections with a 0.008 in. wire in place allow the Onyx or other fluid to "fill" that segment of the vessel at the side hole, forming the "plug"; and will have a wire that will completely obstruct the inner lumen the distal tip of the micro-catheter while Onyx 34 (or equivalent) is injected, preventing obstruction of the distal tip of the micro-catheter from stagnant Onyx that would otherwise be contained in it. In the basic embodiment, if less than two minutes are allowed from initial 'plug' injection until subsequent 'push' injections, the Onyx in the distal tip of the catheter would not normally precipitate fully, and thus does not obstruct the catheter. Alternatively, the inner diameter of the catheter can be constant, and a distal segment of the wire can have a larger outer diameter. In another alternative, the wire and/or catheter can be of consistent diameters throughout, and the wire can have a detachment zone so that a distal segment of the wire, or a "coil" can be detached and left in the distal segment of the catheter, distal to the side hole. The proximal wire can then be removed, and the distal most wire will significantly obstruct flow beyond the side hole and out of the distal end hole until a sufficient plug has been formed and somewhat hardened around the side hole, which would thereby significantly obstruct further flow out of the side hole. This would result in slightly higher-pressure injections resulting in pushing out said distal and now disconnected wire or coil, and then additional liquid embolic can be injected as desired to penetrate a desired lesion being embolized, while said plug already formed prevents reflux of embolic material proximally. In the latter scenario the catheter may optionally be filled with an appropriate liquid embolic solvent prior to initial wire insertion. Nonlimiting examples of such solvents can include DMSO or D5W. For purposes of the present invention, appropriate solvents include DMSO, except for at least one dissolvable region that can comprise a side hole when said solvent is infused and dissolved the structure of at least one region. The wire can then be removed, allowing flow out the tip. In the event that due to some anatomical difficulties, an advancing a wire that far out is not desirable because of tortuosity and frail vessels that can cause perforation of the vessel; in other instances the wire can get stuck in the catheter after injection of Onyx 34, thus preventing the wire's removal and preventing the proper delivery of the Onyx 18 injection. In such cases, alternate embodiments of the present invention should be considered as preferred for those situations.

Referring now to FIG. 3, another embodiment in which the single lumen of the present invention takes the form similar to the design of the distal-most portion of the balloon lumen of the MicroVention Scepter balloon and/or the Micrus/Codman/Depuy Ascent balloon, the portion encompassing the 'valve' beyond the balloon. However, the present invention embodies the general design of the MicroVention Scepter balloon and/or the Micrus/Codman/Depuy Ascent balloon, but as the present invention does not have a balloon, no balloon prep is necessary.

The present invention has a side hole in the lumen whereas the MicroVention Scepter balloon and/or the Micrus/Codman/Depuy Ascent balloon have balloons with a dual lumen design. The preferred embodiment of the present invention has a small channel that can be made at the end of the single lumen catheter, as that which only allows air to go out of it but does not allow contrast out in the Scepter, said channel incorporates one or more elements that allow dimethyl sulfoxide or less viscous Onyx 18 through, but NOT Onyx 34-which would instead flow out of said side hole. In most embodiments the present invention also contains a single lumen. In most embodiments the present invention, the balloon is optional.

As incorporated into the present invention, said mechanism is not dependent upon particle size. The difference between Onyx 34 and Onyx 18 is not related to particle size, but rather the concentration of the suspended material (8% vs. 6%). Thus, the concentration results in different viscosity, but does not differ in particle size, in the various formulations of precipitating hydrophobic inject-able liquid. Nonetheless, other embodiments that utilize particle size differences may be employed as well; optionally employing different embolic materials.

A modification of the second embodiment as described in 00037 uses a particular size/diameter and shape of a channel distal to the side hole that would allow passage of dimethyl sulfoxide (DMSO), and would allow passage of the less viscous embolic agent such as ONYX 18, but would not allow passage of Onyx 34 or the like.

Figure 4:
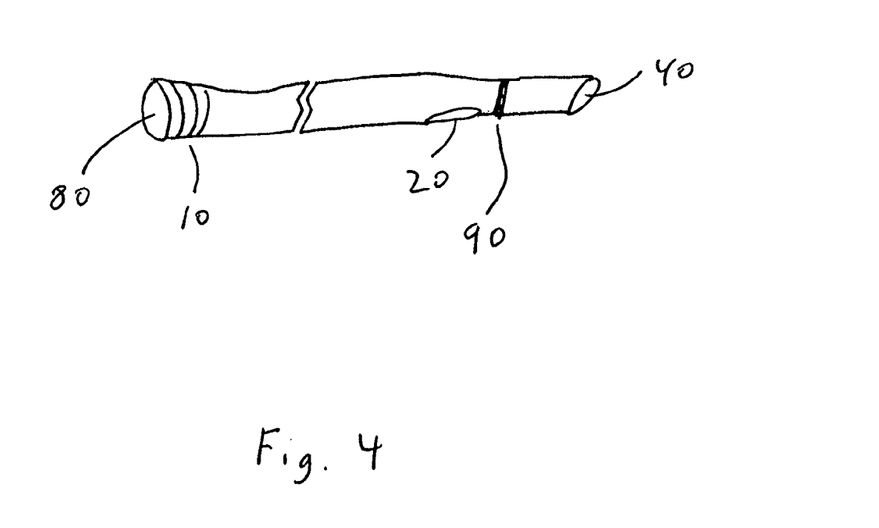
FIG. 4 is a perspective view of the current invention further depicting a governing element proximal to the distal end.

Referring now to FIG. 4, the third embodiment of the present invention is composed of a catheter 10, a side hole 20, a distal end hole 40, a proximal catheter hole 80, and governing element 90. This embodiment a governing element 90 such as a flap valve, a "push" diaphragm, or other device capable of stopping Onyx flow from deploying out of the end hole 40 and thereby diverted to side hole 20. This valve can be positioned anywhere between said side hole and said end hole, in various embodiments, but is optimally immediately distal to the distal end of said side hole. This embodiment may incorporate the design of the Strata® valve, or other valve. Using a standard micro-catheter with a valve on the inner lumen of the micro-catheter at the distal end of the side hole, that can be closed by a magnetic field created by an electric current applied after infusion of dimethyl sulfoxide, or may be closed by opened and closed by alternate mechanisms.

Said valve can be opened by removal of the electric current (after the Onyx 34 or similar is injected and an adequate proximal "plug" is created). In particular, said valve contains a magnet or other means inside the valve mechanism that allows the practitioner to change the opening setting of the valve as desired during a procedure.

Alternatively, non-magnetic micro-value technology may be employed. For example, a solenoid micro-valve may be employed. Said solenoid micro-valves use a coil of wire wound in a helix, like a compressed spring. A magnetic field is created by passing current through the solenoid. The placement of a metallic object within the coil and the ability to vary the current, allows said object to move. In short, a solenoid micro-valve is simply a solenoid with an actuator inside of it. The actuator is situated above the channel of a micro-fluidic device and pushes down on the ceiling of the channel to collapse it and obstruct its flow. Valves opened and closed by other compatible mechanisms can be used as well.

The valve can be semi-permeable/selectively permeable, or non-permeable. Said valve can be fixed and not able to open with selectively permeable material. Any valve which can open does so in response to pressure, magnetic field, or a combination thereof, and/or other triggers.

The third embodiment of the current invention is not anticipated because the Strata® device includes a valve used to regulate the flow of cerebral spinal fluid (CSF) in a shunt system. The embodiment set forth above uses valves to regulate deployment of intravascular liquid embolic agents. Thus, while the Strata® device has some of the same elements as the present invention, said elements are employed for non-obviously different purposes.

In additional embodiments, said valve may be opened by a certain fluid pressure and/or passage of a wire therethrough. Some embodiments may also have a side hole that is covered by a flap or valve that can be opened in a similar fashion. There can be a valve/flap covering said side hole, and an additional valve/flap with the lumen of said catheter, immediately distal to said side hole. This can allow infusion of a solvent with a wire in place, or under sufficient pressure to open both valves, in order to fill the entire catheter with said solvent. Subsequent initial injection of a liquid embolic can then be performed without a wire crossing said inner valve/flap, and under sufficient pressure to open only said side hole valve/flap, but not sufficient pressure to open said inner luminal valve/flap. This would result in initial injections of liquid embolic only out of said side hole, to create an optimal proximal plug. Once a sufficient proximal plug is formed and optionally partially hardened, said plug will also increase resistance to flow out of said side hole. Thereafter, liquid embolic can be injected under higher pressures, opening the intraluminal valve, and allowing flow of liquid embolic through the distal catheter segment, distal to said side hole, and out the distal end hole. Injection can then be continued until desired penetration of a lesion is achieved.

Referring again to FIG. 4, side hole 20 can be governed by the use of a semi-permeable membrane flap across the diameter of the catheter at the distal end of side hole 20. Said semi-permeable membrane is a type of biological or synthetic, polymeric membrane that will allow certain molecules or ions to pass through it by diffusion. In said embodiment, the side-hole closing flap may be used to cover end-hole 40, thus preventing Onyx from deploying through the distal catheter 10 and end hole 40, thereby directing it through side hole 20.

Figure 5:
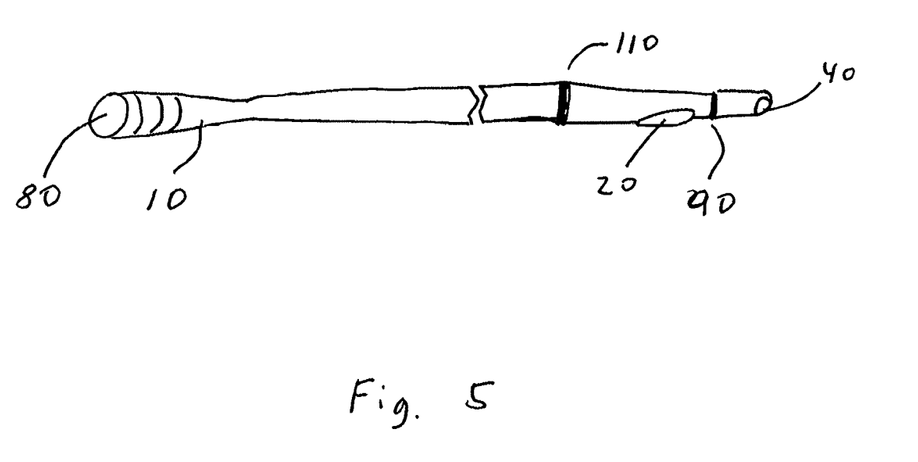
FIG. 5 depicts the embodiment of FIG. 4, further including a breakaway or detachment element proximate to the proximal side of the governing element.

In particular, said flap is placed within the catheter 10 at the distal end of the side hole 20, such that a lumen wire can push it aside, but it will revert to its original (closed) position when said wire is removed. In some embodiments, said flap is permeable to liquid dimethyl sulfoxide, but not to any Onyx, but once a certain pressure is built up from the plug obstructing the side hole, the pressure of the Onyx column will push the flap open, and allow distal flow of Onyx. In other embodiments, the side hole may be covered with a substance that is not compatible with the desired solvent, and infusion of said solvent will cause said side hole covering to dissolve in vivo, thereby opening said side hole. Other methods of opening a side hole cover may be employed as well FIG. 5 shows the embodiment of FIG. 4 with the addition of a detachment element 110 between proximal end hole 80 and side hole 20.

It should be noted that the term governing, as applied to the present invention, comprises a broad range of governing elements, generally distal to the proximal segment, These include anything that can open or close the connection (and flow) between the two segments: including a simple pressure valve, a valve with a different biocompatible solvent, a flap with at least one detachment zone, a controllable valve that can open and close at will, a wire obstruction element, a separate-element detachable DMSO non-compatible detachable plug, an implantable hydrogel plug that can swell and un-swell as desired.

Additionally, the catheter of the present invention may optionally comprise a catheter detachment element, being any element or device capable of making the distal tip of catheter separate from the proximal end.

Alternatively, the present invention incorporates the governor (or valve element) 90 such as that taught by "Bi-stable micro-valve and micro-catheter system" (U.S. Pat. No. 6,663,821 B2) or a similar valve. The present invention in a preferred embodiment employs a bi-stable micro-valve 90 of shape memory material that is operatively connected to a micro-catheter at the distal end of side hole 20. Said bi-stable micro-valve 90 includes tips that can be closed off until said valve 90 is in the desired position. Once it is in position it can be opened and closed. The system uses heat and/or pressure to open and close the micro-valve 90.

Figure 6:
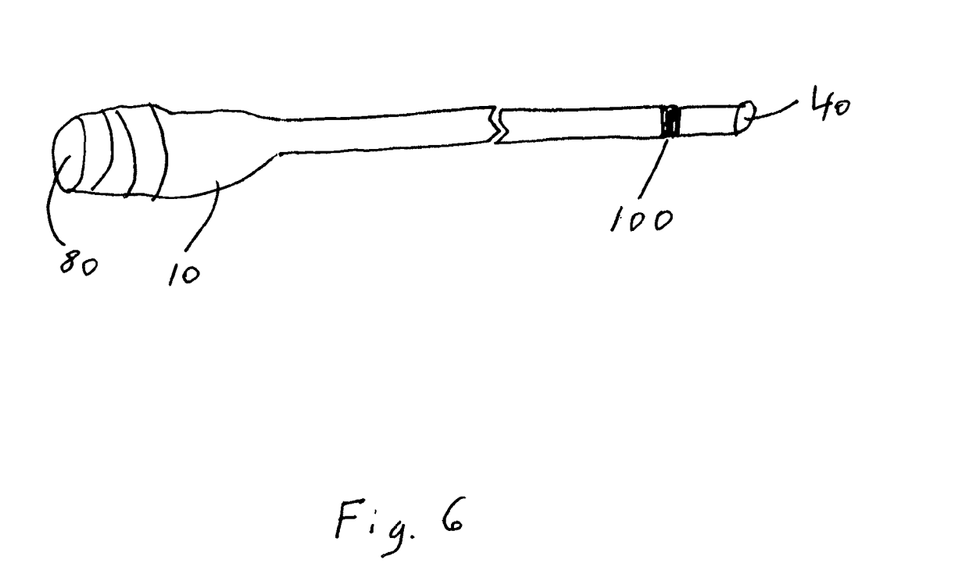
FIG. 6 is a perspective view of an alternate embodiment of the single lumen micro-catheter of the current invention depicting a zone of hydrogel coated on the exterior circumference proximal to the distal end instead of a side hole.

Referring now to FIG. 6, a further embodiment of the present invention is composed of catheter 10, end hole 40, proximal hole 80, and zone of hydrogel 100 coating the exterior circumference of catheter 10 proximal to end hole 40. In this embodiment, no side hole is required. Hydrogel zone 100 extends approximately 1 mm. to 3 cm. from the distal end hole, with a preferred extension of approximately 3 mm. to 10 mm. from the end hole. There may be a gap between said end hole and said hydrogel zone as well, which may be between 0.1 mm and 10 cm long. Said hydrogel can be allowed to swell in vivo, optionally with an additional stimulus. Once fully swollen said hydrogel may occlude said vessel along the hydrogel zone, thereby creating a "proximal plug" and preventing unwanted reflux of liquid embolic, when said liquid embolic is injected through said catheter and out said distal end hole.

Figure 7:
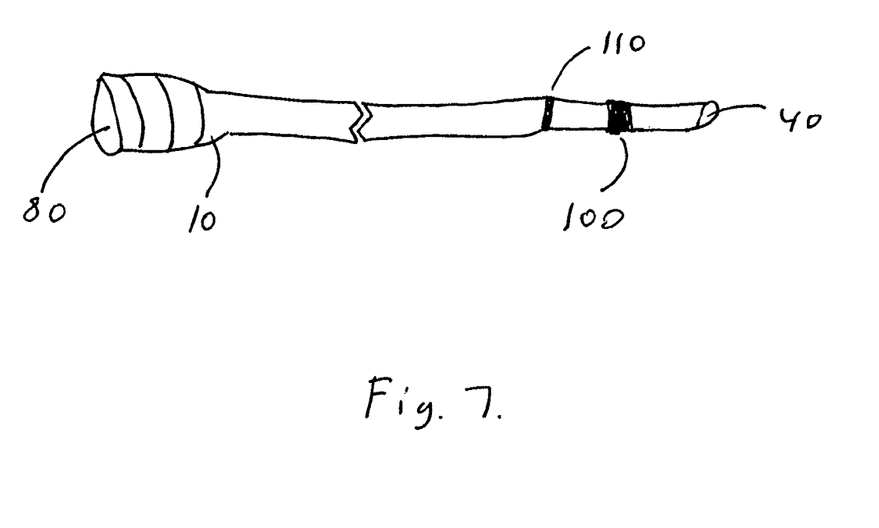
FIG. 7 depicts the embodiment of FIG. 6, further including a breakaway or detachment element 110 proximate to the proximal side of the hydrogel zone.

FIG. 7 shows the embodiment of FIG. 6 with the addition of a detachment element 110 proximate to the proximal extent hydrogel zone 100.

The various embodiments of the present invention may be used by employing one or more of the following methods:

A method is disclosed for using the catheter for endovascular treatment of arteriovenous malformations and arteriovenous fistulas, comprising the steps of:
(a) inserting said catheter with governing element in open (flow-through) position;
(b) advancing said catheter to a target vessel proximal to a target lesion;
(c) injecting a liquid embolic solvent into said catheter;
(d) closing said governing element;
(e) injecting a liquid embolic, which exits said side-hole, to form a plug around said side hole between said detachment zone and said distal end hole
(f) stopping injection when opening of side hole is covered adequately with liquid embolic, and when adjacent vessel lumen is obstructed by said plug;
(g) waiting until said plug is at least partially solidified
(h) opening said governing element
(i) injecting additional said liquid embolic until achieving desired penetration of said target lesion;
(j) stopping injection when optimal amount of said liquid embolic is present in said lesion; and
(k) removing said catheter from its proximal end, optionally detaching said distal catheter at said detachment zone during removal of proximal microcatheter.

Alternatively:

A method is disclosed for using the catheter of the present invention embodiment for endovascular treatment of a lesion, wherein a governing element is capable of opening and closing the connection between the continuous inner lumen of the proximal segment and the distal segment, comprising the steps of:
(a) inserting said catheter with governing element in open (flow-through) position;
(b) advancing said catheter to a target vessel proximal to a target lesion;
(c) injecting an appropriate liquid embolic solvent into said catheter to fill said catheter
(e) closing governing element;
(f) injecting liquid embolic to form a plug around said side hole between said detachment zone (when present) and said distal end hole
(g) stopping injection when side hole is covered adequately with liquid embolic, and when adjacent vessel lumen is substantially obstructed by said plug;
(h) waiting until said plug is partially solidified
(i) opening said governing element
(j) injecting additional said liquid embolic to penetrate said target lesion;
(k) stopping injection when optimal amount of said liquid embolic is present in said lesion; and
(l) removing said catheter from proximal end, while optionally simultaneously detaching the distal portion of said catheter at said detachment zone when present).

Alternatively:

A method of using the catheter of the present invention for endovascular treatment of a lesion, further comprising a detachment zone distal to said proximal hole, and proximal to said at least one side hole, said method comprising the steps of:
(a) inserting said catheter;
(b) advancing said catheter to a target vessel proximal to a target lesion;
(c) optionally injecting a liquid embolic solvent through the length of said catheter,
(d) advancing a wire with a distal detachable tip the same length of distance between the distal end of said side-hole and said distal end-hole
(e) detaching said distal end of said wire, and removing the proximal end of said wire
(f) optionally injecting a liquid embolic solvent through the length of said catheter
(g) injecting a liquid embolic to form a plug around said side hole between said detachment zone (when present) and said distal end hole, said catheter distal to said side hole being substantially obstructed by said detached distal wire, thereby obstructing flow of liquid embolic through said distal catheter segment and out said distal end hole;
(h) waiting until said plug is partially solidified
(i) injecting additional said liquid embolic, with said plug at said side hole now having higher resistance then said wire in said distal catheter, causing said additional liquid embolic injection to push out said detached wire segment through said end hole
(j) continuing liquid embolic injection until desired penetration of said target lesion is achieved;
(k) stopping injection when optimal amount of said liquid embolic is present in said lesion; and
(l) removing said catheter from its proximal end, optionally detaching said distal catheter at said detachment zone, when present, during removal of proximal microcatheter.

Although the invention has been described in detail in the foregoing embodiments for the purpose of illustration, it is to be understood that such detail is solely for that purpose, and that variations can be made therein by those skilled in the art without departing from the spirit and scope of the invention, except as it may be described by the following claims.

I claim:
1. A catheter for delivering a liquid embolic agent to form a plug, the catheter comprising:
an elongated tube having a lumen extending therethrough and a distal end hole in communication with the lumen;
at least one side hole positioned proximal of the distal end hole and in communication with the lumen;
a proximal hole in communication with the lumen through which the liquid embolic agent is injected;
a proximal segment positioned proximal of the at least one side hole, the proximal hole positioned in the proximal segment;
a distal segment, the at least one side hole positioned in the distal segment;
a detachment zone proximal to the distal end hole for detaching the distal segment from the proximal segment after formation of the plug;
wherein the catheter includes flow restricting structure configured to temporarily restrict flow through the lumen distal of the at least one side hole for formation of the plug from the liquid embolic agent adjacent the at least one side hole and proximal of the distal end hole.

2. The catheter of claim 1, wherein the catheter has only a single lumen.

3. The catheter of claim 1, wherein the flow restricting structure comprises a valve, the valve restricting flow distal of the at least one side hole.

4. The catheter of claim 1, wherein the catheter has a reduced inner diameter distal of the at least one side hole so the inner diameter is greater in the proximal segment than in the distal segment, the reduced inner diameter restricting flow distal of the at least one side hole.

5. The catheter of claim 1, wherein the flow restricting structure comprises a wire extending distal of the at least one side hole to restrict flow distal of the at least one side hole.

6. The catheter of claim 5, wherein the wire is removable to enable flow through the distal end hole after the plug is formed adjacent the at least one side hole.

7. The catheter of claim 5, wherein the wire has a detachment zone detachable to separate a distal portion of the wire from a proximal portion of the wire.

8. The catheter of claim 7, wherein the wire is detachable along with the distal segment of the catheter.

9. The catheter of claim 1, wherein the distal end of the catheter is tapered.

10. The catheter of claim 1, wherein the detachment zone includes a breakaway element comprising a score or a stressed area.

11. The catheter of claim 5, wherein a diameter of a distal segment of the wire is greater than a proximal segment.

12. The catheter of claim 1, wherein the flow restricting structure comprises a coil in the distal segment distal of the at least one side hole, the coil remaining within the distal segment when detached from the proximal segment.

13. The catheter of claim 1, wherein the liquid embolic agent has a first viscosity and the distal segment has a channel to allow passage of an embolic agent having a second viscosity and prevent passage of embolic liquid of the first viscosity.

14. The catheter of claim 1, wherein the distal segment has a channel configured to allow passage of air and DMSO but prevent passage of Onyx 34.

15. The catheter of claim 5, further comprising a valve positioned between the at least one side hole and distal end hole.

16. The catheter of claim 15, wherein the valve is closed by a magnetic field.

17. The catheter of claim 15, wherein the valve is closed by an electric current.

18. The catheter of claim 1, further comprising a valve positioned over the at least one side hole openable by fluid pressure.

19. The catheter of claim 1, further comprising a membrane covering the distal end hole.

20. The catheter of claim 1, wherein said at least one side hole is flush with an outer surface of said elongated tube.

21. A catheter for delivering a liquid embolic agent to form a plug, the catheter comprising:
  an elongated tube having a lumen extending therethrough and a distal end hole in communication with the lumen;
  at least one side hole formable proximal of the distal end hole and in communication with the lumen, the at least one side hole configured for passage of a liquid embolic agent;
  a proximal hole in communication with the lumen through which the liquid embolic agent is injected;
  a proximal segment, the proximal hole positioned in the proximal segment;
  a distal segment, the distal end hole positioned in the distal segment; and
  a detachment zone proximal to the distal end hole for detaching the distal segment from the proximal segment after formation of the plug;
  wherein the catheter includes a covering to cover the at least one side hole which dissolves to open the at least one side hole for passage of the agent, the covering dissolved by infusion of the agent to contact the covering.

22. The catheter of claim 21, further comprising a flow restriction structure within the catheter to restrict flow of the liquid embolic agent distal of the at least one side hole for exit through the at least one side hole after the covering is dissolved by the agent.

23. The catheter of claim 22, wherein the flow restriction structure comprises a valve positioned between the at least one side hole and distal end hole.

24. The catheter of claim 21, further comprising a valve positioned over the at least one side hole.

* * * * *